United States Patent [19]

Riebel et al.

[11] 4,053,594
[45] Oct. 11, 1977

[54] O-ALKYL-O-[4,6-DIMETHYL-5-CHLOROPYRIMIDIN-(2)-YL]-(THIONO)(THIOL) PHOSPHORIC ACID ESTERS

[75] Inventors: Hans-Jochem Riebel, Wuppertal; Bernhard Homeyer, Leverkusen; Ingeborg Hammann, Cologne, all of Germany

[73] Assignee: Bayer Aktiengesellschaft, Leverkusen, Germany

[21] Appl. No.: 624,219

[22] Filed: Oct. 20, 1975

[30] Foreign Application Priority Data

Oct. 26, 1974 Germany .................. 2450951

[51] Int. Cl.$^2$ ............... A01N 9/36; C07D 239/34
[52] U.S. Cl. ............... 424/200; 260/251 P; 260/256.4 E; 260/256.5 R
[58] Field of Search ............... 260/251 P; 424/200

[56] References Cited

U.S. PATENT DOCUMENTS

| | | | |
|---|---|---|---|
| 3,313,814 | 4/1967 | Thompson et al. | 260/251 P X |
| 3,741,968 | 6/1973 | Haubein | 260/251 P |
| 3,823,235 | 7/1974 | Haubein | 424/400 |

Primary Examiner—Donald G. Daus
Assistant Examiner—D. B. Springer
Attorney, Agent, or Firm—Burgess, Dinklage & Sprung

[57] ABSTRACT

O-Alkyl-O-[4,6-dimethyl-5-chloropyrimidin(2)-yl]-(thiono) (thiol) phosphoric acid esters and ester-amides of the formula

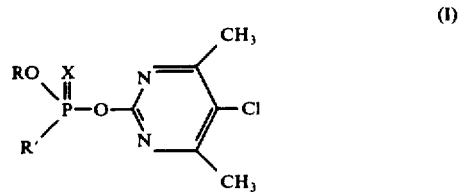

(I)

in which
R is alkyl with 1 to 6 carbon atoms,
R' is alkoxy, alkylthio, monoalkylamino or dialkylamino, with 1 to 6 carbon atoms in each alkyl chain, and
X is oxygen or sulfur,
which possess insecticidal, acaricidal and nematicidal properties.

10 Claims, No Drawings

O-ALKYL-O-[4,6-DIMETHYL-5-CHLOROPYRIMI-DIN-(2)-YL]-(THIONO) (THIOL) PHOSPHORIC ACID ESTERS

The present invention relates to and has for its objects the provision of particular new O-alkyl-O-[4,6-dimethyl-5-chloropyrimidin(2)yl]-(thiono) (thiol) phosphoric acid esters and ester-amides, which possess insecticidal, acaricidal and nematicidal properties, active compositions in the form of mixtures of such compounds with solid and liquid dispersible carrier vehicles, and methods for producing such compounds and for using such compounds in a new way especially for combating pests, e.g., insects, acarids and nematodes, with other and further objects becoming apparent from a study of the within specification and accompanying examples.

It is known from U.S. Pat. No. 3,741,968 and German DOS No. 2,144,392 that pyrimidinyl(thiono)phosphoric acid esters and ester-amides, for example, O,O-dimethyl(Compound A) and O,O-diethyl-O-pyrimidin(2)yl-thionophosphoric acid esters (Compound B) or O,O-diethyl-O-[2,4-dimethyl-5-methylmercapto-pyrimidin(6)yl]-phosphoric acid ester (Compound C) and -thionophosphoric acid ester (Compound D) or O-methyl-O-[2,4-dimethyl-5-methylmercap-topyrimidin(6)yl]-N-isopropylthionophosphoric acid ester-amide (Compound E), have insecticidal and acaricidal properties.

The present invention provides, as new compounds, the pyrimidinyl(thiono) (thiol)phosphoric (phosphonic) acid esters and ester-amides of the general formula

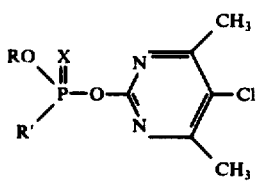

(I)

in which
R is alkyl with 1 to 6 carbon atoms,
R' is alkoxy, alkylthio, monoalkylamino or dialkyl-amino, with 1 to 6 carbon atoms in each alkyl chain, and
X is oxygen or sulfur.

Preferably R is straight-chain or branched alkyl with 1 to 4 carbon atoms, and R' is straight-chain or branched alkoxy with 1 to 5 carbon atoms or straight-chain or branched alkylthio or monoalkylamino with 1 to 4 carbon atoms.

Surprisingly, the pyrimidinyl(thiono)(thiol)phosphoric (phosphonic) acid esters and ester-amides according to the invention exhibit a better insecticidal, acaricidal and nematicidal action than the corresponding previously known compounds of analogous structure and of the same type of action. Accordingly, the products according to the present invention represent a genuine enrichment of the art.

The present invention also provides a process for the preparation of a pyrimidinyl(thiono)(thiol)phosphoric(-phosphonic) acid ester or ester-amide of the formula (I), in which a (thiono)(thiol)phosphoric(phosphonic) acid ester halide or ester-amide halide of the general formula (II),

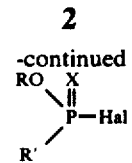

in which
R, R' and X have the above-mentioned meanings, and
Hal is halogen, especially chlorine, is reacted, if appropriate in the presence of a solvent or diluent, with the free base or the hydrochloride of 2-hydroxy-4,6-dimethyl-5-chloro-pyrimidine of the formula

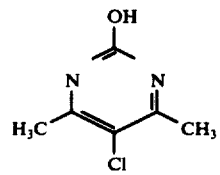

(III), if appropriate in the presence of acid acceptors, or with an alkali metal salt, alkaline earth metal salt or ammonium salt of the free base.

If, for example, N,N-dimethyl-O-ethyl-phosphoric acid ester-amide chloride and the hydrochloride of 2-hydroxy-4,6-dimethyl-5-chloropyrimidine are used as starting materials, the course of the reaction can be represented by the following equation:

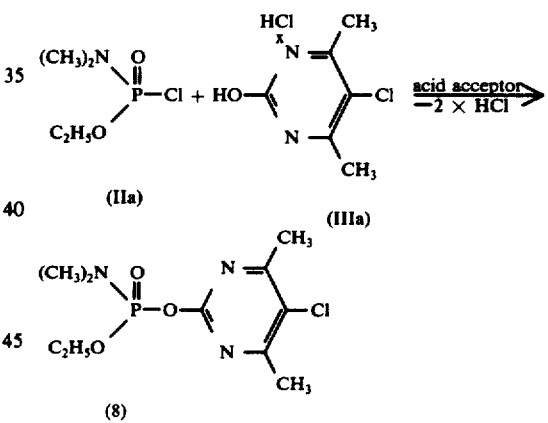

The (thiono)(thiol)phosphoric(phosphonic) acid ester halides and ester-amide halides (II) are known from the literature and can be prepared in accordance with generally customary methods. The following may be mentioned as examples thereof: O,O-dimethyl-, O,O-diethyl-, O,O-di-n-propyl, O,O-di-isopropyl-, O,O-di-n-butyl-, O,O-di-isobutyl, O,O-di-sec.-butyl-, O,O-di-tert.-butyl-, O-ethyl-O-n-propyl-, O-ethyl-O-isopropyl-, O-n-butyl-O-ethyl-, O-ethyl-O-sec.-butyl-, O-ethyl-O-methyl-, O-ethyl-O-pentyl-, O-n-propyl-O-pentyl- and O-isopropyl-O-pentyl-phosphoric acid diester chlorides and the corresponding thiono analogues; O,S-dimethyl-, O,S-diethyl-, O,S-di-n-propyl-, O,S-di-isopropyl-, O,S-di-n-butyl-, O,S-di-isobutyl-, O,S-di-tert.-butyl-, O-ethyl-S-n-propyl-, O-ethyl-S-isopropyl, O-ethyl-S-n-butyl-, O-ethyl-S-sec.-butyl-, O-n-propyl-S-ethyl-, O-n-propyl-S-isopropyl-, O-n-butyl-S-n-propyl- and O-sec.-butyl-S-ethyl-thiolphosphoric acid diester chlorides and the corresponding thiono analogues; and O-methyl-N- methyl, O-ethyl-N-methyl-, O-n-propyl-N-methyl-, O-isopropyl-N-methyl-, O-n-butyl-N-methyl-, O-sec.-butyl-N-methyl-, O-methyl-N-ethyl-, O-ethyl-N-ethyl-, O-n-propyl-N-ethyl-, O-isopropyl-N-ethyl-, O-n-butyl-N-ethyl-, O-sec.-butyl-N-ethyl-, O-methyl-N-n-propyl-, O-ethyl-N-n-propyl-, O-n-propyl-N-n-propyl-, O-n-propyl-N-n-butyl-, O-isopropyl-N-ethyl-, O-isopropyl-N-n-butyl- and O-tert.-butyl-N-ethyl-phosphoric acid ester-amide chlorides and the corresponding thiono analogues.

The hydrochloride of 2-hydroxy-4,6-dimethyl-5-chloropyrimidine can be prepared according to generally customary methods known from the literature, by reacting 3-chloropentane-2,4-dione and urea in alcoholic solution in the presence of concentrated hydrochloric acid.

The process of preparation of the present compounds is preferably carried out in the presence of suitable solvents and diluents. As such it is possible to use practically all inert organic solvents, especially aliphatic and aromatic, optionally chlorinated hydrocarbons, such as benzene, toluene, xylene, benzine, methylene chloride, chloroform, carbon tetrachloride and chlorobenzene; ethers, for example diethyl ether, dibutyl ether and dioxane; ketones, for example acetone, methyl ethyl ketone, methyl isopropyl ketone and methyl isobutyl ketone; and nitriles, such as acetonitrile and propionitrile.

As acid acceptors, it is possible to use all customary acid-binding agents. Alkali metal carbonates and alkali metal alcoholates, such as sodium carbonate and potassium carbonate and potassium t-butylate, have proved particularly successful, as have aliphatic, aromatic or heterocyclic amines, for example triethylamine, trimethylamine, dimethylaniline, dimethylbenzylamine and pyridine.

The reaction temperature can be varied within a fairly wide range. In general, the reaction is carried out at between 0° and 100° C, preferably at from 30° to 50° C.

The reaction is in general allowed to take place under normal pressure.

In carrying out the process according to the invention, the reactants are in general employed in equimolar amounts. An excess of one or other component produces no significant advantages. The reaction is preferably carried out in the presence of an acid acceptor and in the presence of one of the above-mentioned solvents and diluents, at the temperatures indicated. After a reaction time of one or more hours, the reaction mixture is worked up in the usual manner by pouring it into an organic solvent, for example toluene, extracting the mixture by shaking with water, separating off the organic phase and drying it, and distilling off the solvent.

The new compounds are obtained in the form of oils which cannot be distilled without decomposition but are freed from the last volatile constituents by so-called "slight distillation," that is to say by prolonged heating under reduced pressure to moderately elevated temperatures and are purified in this way. They are characterized by the refractive index.

As already mentioned, the pyrimidinyl(thiono)(thiol) phosphoric(phosphonic) acid esters and ester-amides according to the invention are distinguished by an outstanding insecticidal, acaricidal and nematicidal activity. They are active against plant pests, pests harmful to health and pests of stored products. They combine a low phytotoxicity with a good action against both sucking and biting insects and against mites.

For this reason, the compounds according to the invention can be employed successfully as pesticides in plant protection and in the hygiene field and the field of protection of stored products.

The active compounds according to the invention show good toleration by plants and a favorable level of toxicity to warm-blooded animals and are suitable for combating all stages of development, or individual stages of development, including the pre-embryonic normally sensitive and resistant stages of development, of arthropods or nematodes, where these are known as pests in agriculture, in forestry, in protection of stored products and of materials, and in the hygiene field.

The economically important pests in agriculture and forestry, pests of stored products, pests destructive of materials and pests harmful to health include: from the order of the Isopoda, for example, *Oniscus asellus, Armadillidium vulgare* and *Porcellio scaber;* from the order of the Diplopoda, for example, *Blaniulus guttulatus;* from the order of the Chilopoda, for example, *Geophilus carpophagus* and *Scutigera* spec.; from the order of the Symphyla, for example, *Scutigerella immaculata;* from the order of the Arachnida, for example, *Scorpio maurus* and *Latrodectus mactans;* from the order of Acarina, for example, *Acarus siro, Argas reflexus, Ornithodoros moubata, Dermanyssus gallinae, Eriophyes ribis, Phyllocoptruta oleivora, Boophilus microplus, Rhipicephalus evertsi, Sarcoptes scabiei, Tarsonemus* spec., *Bryobia praetiosa, Panonychus citri, Panonychus ulmi, Tetranychus tumidus* and *Tetranychus urticae;* from the order of the Thysanura, for example, *Lepisma saccharina;* from the order of the Collembola, for example, *Onychiurus armatus;* from the order of the Orthoptera, for example, *Blatta orientalis Periplaneta americana, Leucophaea maderae, Blattella germanica, Acheta domesticus, Gryllotalpa* spec., *Locusta migratoria migratorioides. Melanoplus differentialis* and *Schistocerca gregaria;* from the order of the Dermaptera, for example, *Forficula auricularia;* from the order of the Isoptera, for example, *Reticulitermes* spec.; from the order the Anoplura, for example, Phylloxera vastatrix, Pemphigus spec. and *Pediculus humanus corporis;* from the order of the Thysanoptera, for example, *Hercinothrips femoralis* and *Thrips tabaci;* from the order of the Heteroptera, for example, *Eurygaster* spec., *Dysdercus intermedius, Piesma quadrata, Cimex lectularius, Rhodnius prolixus* and *Triatoma* spec.; from the order of the Homoptera, for example, *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae, Myzus cerasi, Myzus persicae, Phorodon humuli, Rhopalosiphum padi, Empoasca* spec., *Euscelis bilobatus, Nephotettix cincticeps, Lecanium corni, Saissetia oleae, Laodelphax striatellus, Nilaparvata lugens, Aonidiella aurantii, Aspidiotus hederae, Pseudococcus* spec. and Psylla spec.; from the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea, Lymantria* spec., *Bucculatrix thurberiella, Phyllocnistic citrella, Agrotis* spec., *Euxoa* spec., *Feltia* spec., *Earias insulana, Heliothis* spec., *Laphygma exigua, Mamestra brassicae, Panolis flammea, Prodenia litura, Spodoptera* spec., *Tri-*

*choplusia ni, Carpocapsa pomonella, Pieris* spec., *Chilo* spec., *Pyrausta nubilalis, Ephestia kühniella, Galleria mellonella, Cacoecia podana, Capua reticulana, Choristoneura fumiferana, Clysia ambiguella, Homona magnanima* and *Tortrix viridana;* from the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae, Diabrotica* spec., *Pyslliodes chrysocephala, Epilachna varivestis, Atomaria* spec., *Oryzaephilus surinamensis, Anthonomus* spec., *Sitophilus* spec., *Otiorrhynchus sulcatus, Cosmopolites sordidus, Ceuthorrhynchus assimilis, Hypera postica, Dermestes* spec., *Trogoderma* spec., *Anthrenus* spec., *Attagenus* spec., *Lyctus* spec., *Meligethes aeneus, Ptinus* spec., *Niptus holoeucus, Gibbium psylloides, Tribolium* spec., *Tenebrio molitor, Agriotes* spec., *Conoderus* spec., *Melolontha melolontha, Amphimallus solstitialis* and *Costelytra zealandica;* from the order of the Hymenoptera, for example, *Diprion* spec., *Hoplocampa* spec., *Lasius* spec., *Monomorium pharaonis* and *Vespa* spec.; from the order of the Diptera, for example, *Aëdes* spec., *Anopheles* spec., *Culex* spec., *Drosophila melanogaster, Musca domestica, Fannia* spec., *Stomoxys calcitrans, Hypoderma* spec., *Bibio hortulanus, Oscinella frit, Phorbia* spec., *Pegomyia hyoscyami, Calliphora erythrocephala, Lucilia* spec., *Chrysomyia* spec., *Ceratitis capitata, Dacus oleae* and *Tipula paludosa;* and from the order of the Siphonaptera, for example, *Xenopsylla cheopis.*

When used against pests harmful for health and pests of stored products, the active compounds are distinguished by an excellent residual action on wood and clay and good stability to alkali on limed substrates.

The active compounds according to the instant invention can be utilized, if desired, in the form of the usual formulations or compositions with conventional inert (i.e., plant compatibile or herbicidally inert) pesticide diluents or extenders, i.e., diluents, carriers or extenders of the type usable in conventional pesticide formulations or compositions, e.g., conventional pesticide dispersible carrier vehicles such as gases, solutions, emulsions, suspensions, emulsifiable concentrates, spray powders, pastes, soluble powders, dusting agents, granules, etc. These are prepared in known manner, for instance by extending the active compounds with conventional pesticide dispersible liquid diluent carriers and/or dispersible solid carriers optionally with the use of carrier vehicle assistants, e.g., conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as Freon; inert dispersible liquid diluent carriers, including inert organic solvents, such as aromatic hydrocarbons (e.g., benzene, toluene, xylene, alkyl naphthalenes, etc.), halogenated, especially chlorinated, aromatic hydrocarbons (e.g., chlorobenzenes, etc.), cycloalkanes, (e.g., cyclohexane, etc.), paraffins (e.g., petroleum or mineral oil fractions), chlorinated aliphatic hydrocarbons (e.g., methylene chloride, chloroethylenes, etc.), alcohols (e.g., methanol, ethanol, propanol, butanol, glycol, etc.) as well as ethers and esters thereof (e.g., glycol monomethyl ether, etc.), amines (e.g., ethanolamine, etc.), amides (e.g., dimethyl formamide, etc.), sulfoxides (e.g., dimethyl sulfoxide, etc.), acetonitrile, ketones (e.g., acetone, methyl ethyl ketone, methyl isobutyl ketone, cyclohexanone, etc.), and/or water; as well as inert dispersible finely divided solid carriers, such as ground natural minerals (e.g., kaolins, clays, alumina, silica, chalk, i.e., calcium carbonate, talc, attapulgite, montmorillonite, kieselguhr, etc.) and ground synthetic minerals (e.g., highly dispersed silicic acid, silicates, e.g., alkali silicates, etc.); whereas the following may be chiefly considered for use as conventional carrier vehicle assistants, e.g., surface-active agents, for this purpose: emulsifying agents, such as non-ionic and/or anionic emulsifying agents (e.g., polyethylene oxide esters of fatty acids, polyethylene oxide ethers of fatty alcohols, alkyl sulfates, alkyl sulfonates, aryl sulfonates, albumin hydrolyzates, etc., and especially alkyl arylypolyglycol ethers, magnesium stearate, sodium oleate, etc.); and/or dispersing agents, such as lignin, sulfite waste liquors, methyl cellulose, etc.

Such active compounds may be employed alone or in the form of mixtures with one another and/or with such solid and/or liquid dispersible carrier vehicles and/or with other known compatible active agents, especially plant protection agents, such as other insecticides, acaricides and nematicides, or fungicides, bactericides, rodenticides, herbicides, fertilizers, growth-regulating agents, etc., if desired, or in the form of particular dosage preparations for specific application made therefrom, such as solutions, emulsions, suspensions, powders, pastes, granules, very fine capsules in polymeric substances and in coating compositions suited for use on seed, and fumigating cartridges.

As concerns commercially marketed preparations, these generally contemplate carrier composition mixtures in which the active compound is present in an amount substantially between about 0.1-95% by weight, and preferably 0.5-90% by weight, of the mixture, whereas carrier composition mixtures suitable for direct application or field application generally contemplate those in which the active compound is present in an amount substantially between about 0.0001-10%, preferably 0.01-1%, by weight of the mixture. Thus, the present invention contemplates overall compositions which comprise mixtures of a conventional dispersible carrier vehicle such as (1) a dispersible inert finely divided carrier solid, and/or (2) a dispersible carrier liquid such as an inert organic solvent and/or water, preferably including a surface-active effective amount of a carrier vehicle assistant, e.g., a surface-active agent, such as an emulsifying agent and/or a dispersing agent, and an amount of the active compound which is effective for the purpose in question and which is generally between about 0.0001-95%, and preferably 0.01-95%, by weight of the mixture.

The active compounds can also be used in accordance with the well known ultra-low-volume process with good success, i.e., by applying such compound if normally a liquid, or by applying a liquid composition containing the same, via very effective atomizing equipment, in finely divided form, e.g., average particle diameter of from 50-100 microns, or even less, i.e., mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g., about 20-100% by weight of the active compound.

When used against nematodes, the preparations are generally applied to an area of agriculture in amounts of 1 to 100 kg of active compound per hectare, and are then incorporated into the soil.

Furthermore, the present invention contemplates methods of selectively killing, combating or controlling pests, e.g., insects, acarids and nematodes, which comprises applying to at least one of correspondingly (a) such insects, (b) such acarids, (c) such nematodes, and (d) the corresponding habitat thereof, i.e., the locus to be protected, e.g., to a growing crop, to an area where a crop is to be grown or to a domestic animal, a correspondingly combative or toxic amount, i.e., an insecticidally, acaricidally or nematocidally effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, dressing, encrusting, and the like.

It will be realized, of course, that the concentration of the particular active compound utilized in admixture with the carrier vehicle will depend upon the intended application. Therefore, in special cases it is possible to go above or below the aforementioned concentration ranges.

The unexpected superiority and outstanding activity of the particular new compounds of the present invention are illustrated, without limitation, by the following examples:

EXAMPLE 1

Tetranychus test (resistant)

Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Bean plants (*Phaseolus vulgaris*), which had a height of approximately 10-30 cm, were sprayed with the preparation of the active compound until dripping wet. These bean plants were heavily infested with the two-spotted spider mite (*Tetranychus urticae*) in all stages of development.

After the specified periods of time, the degree of destruction was determined as a percentage: 100% means that all the spider mites were killed whereas 0% means that none of the spider mites were killed.

The active compounds, the concentrations of the active compounds, the evaluation times and the results can be seen from the following table:

Table 1

| (*Tetranychus* test) | | |
|---|---|---|
| Active compound | Active compound conc. in % | Degree of destruction in % after 2 days |
| 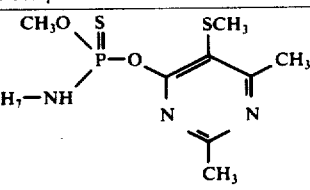 (known) (E) | 0.1 | 0 |
| 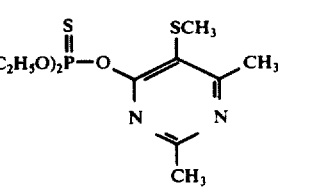 (known) (D) | 0.1 | 0 |
| 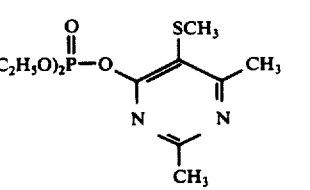 (known) (C) | 0.1 | 0 |
| 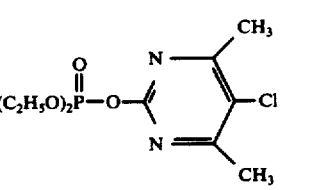 (5) | 0.1 | 98 |
| 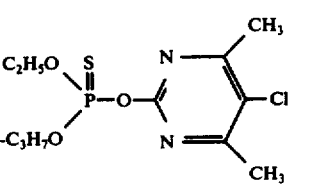 (2) | 0.1 | 90 |
| 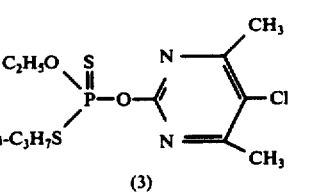 (3) | 0.1 | 100 |

EXAMPLE 2

Laphygma test

Solvent: 3 parts by weight of acetone
Emulsifier: 1 part by weight of alkylaryl polyglycol ether To produce a suitable preparation of active compound, 1 part by weight of the active compound was mixed with the stated amount of solvent and the stated amount of emulsifier and the concentrate was diluted with water to the desired concentration.

Cotton leaves (*Gossypium hirsutum*) were sprayed with the preparation of the active compound until dew-moist and were then infested with caterpillars of the owlet moth (*Laphygma exigua*).

After the specified periods of time, the destruction in % was determined. 100% means that all the caterpillars had been killed, whereas 0% indicates that no caterpillars had been killed.

The active compounds, the concentrations of the active compound, the evaluation times and the results can be seen from the following table:

Table 2

| Active compound | Active compound concentration in % | Degree of destruction in % after 3 days |
|---|---|---|
| (CH$_3$O)$_2$P(S)—O—[pyrimidine] (known) (A) | 0.01<br>0.001 | 100<br>0 |
| (C$_2$H$_5$O)$_2$P(S)—O—[pyrimidine] (known) (B) | 0.01<br>0.001 | 100<br>0 |
| CH$_3$O, n-C$_3$H$_7$O—P(S)—O—[4-Cl-5,6-dimethylpyrimidine] (6) | 0.01<br>0.001 | 100<br>100 |
| CH$_3$O, n-C$_4$H$_9$O—P(S)—O—[4-Cl-5,6-dimethylpyrimidine] (7) | 0.01<br>0.001 | 100<br>70 |
| C$_2$H$_5$O, n-C$_3$H$_7$O—P(S)—O—[4-Cl-5,6-dimethylpyrimidine] (2) | 0.01<br>0.001 | 100<br>80 |

EXAMPLE 3

Plutella test

Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage leaves (*Brassica oleracea*) were sprayed with the preparation of the active compound until dew moist and were then infested with caterpillars of the diamond-back moth (*Plutella maculipennis*).

After the specified periods of time, the degree of destruction was determined as a percentage: 100% means that all the caterpillars were killed whereas 0% means that none of the caterpillars were killed.

The active compounds, the concentrations of the active compounds, the evaluation times and the results can be seen from the following table:

Table 3
(*Plutella* test)

| Active compound | Active compound conc. in % | Degree of destruction in % after 3 days |
|---|---|---|
| CH$_3$O, iso-C$_3$H$_7$—NH—P(S)—O—[SCH$_3$, CH$_3$, isopropyl-pyrimidine] (known) (E) | 0.1 | 20 |
| (C$_2$H$_5$O)$_2$P(S)—O—[SCH$_3$, CH$_3$, isopropyl-pyrimidine] (known) (D) | 0.1<br>0.01 | 100<br>0 |
| (C$_2$H$_5$O)$_2$P(O)—O—[SCH$_3$, CH$_3$, isopropyl-pyrimidine] (known) (C) | 0.1<br>0.01 | 100<br>0 |
| CH$_3$O, n-C$_3$H$_7$O—P(S)—O—[4-Cl-5,6-dimethylpyrimidine] (6) | 0.1<br>0.01 | 100<br>100 |
| CH$_3$O, n-C$_4$H$_9$O—P(S)—O—[4-Cl-5,6-dimethylpyrimidine] (7) | 0.1<br>0.01 | 100<br>100 |
| (C$_2$H$_5$O)$_2$P(S)—O—[4-Cl-5,6-dimethylpyrimidine] (1) | 0.1<br>0.01 | 100<br>100 |
| (C$_2$H$_5$O)$_2$P(O)—O—[4-Cl-5,6-dimethylpyrimidine] (5) | 0.1<br>0.01 | 100<br>100 |

11

Table 3-continued
(Plutella test)

| Active compound | Active compound conc. in % | Degree of destruction in % after 3 days |
|---|---|---|
| (2) C₂H₅O–P(=S)(–O–[pyrimidine: 4-CH₃, 5-Cl, 6-CH₃])–O–n-C₃H₇ | 0.1<br>0.01 | 100<br>100 |
| (3) C₂H₅O–P(=S)(–O–[pyrimidine: 4-CH₃, 5-Cl, 6-CH₃])–S–n-C₃H₇ | 0.1<br>0.01 | 100<br>100 |

EXAMPLE 4
Drosophila test

Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier, and the concentrate was diluted with water to the desired concentration.

1 ml of the preparation of the active compound was applied with a pipette to a filter paper disc of 7 cm diameter. The wet disc was placed over the orifice of a glass vessel containing 50 vinegar flies (*Drosophila melanogaster*) and covered with a glass plate.

After the specified periods of time, the destruction was determined in %. 100% means that all flies were killed; 0% means that no flies were killed.

The active compounds, the concentrations of the active compounds, the evaluation times and the results can be seen from the following table:

Table 4
(Drosophila test)

| Active compound | Active compound conc. in % | Degree of destruction in % after 1 day |
|---|---|---|
| (known) (C) (C₂H₅O)₂P(=O)–O–[pyrimidine with SCH₃, CH₃, CH₃] | 0.1<br>0.01 | 100<br>20 |
| (known) (E) CH₃O–P(=S)(–O–[pyrimidine with SCH₃, CH₃, CH₃])–NH–iso-C₃H₇ | 0.1<br>0.01 | 100<br>0 |

Table 4-continued
(Drosophila test)

| Active compound | Active compound conc. in % | Degree of destruction in % after 1 day |
|---|---|---|
| (6) CH₃O–P(=S)(–O–[pyrimidine: 4-CH₃, 5-Cl, 6-CH₃])–O–n-C₃H₇ | 0.1<br>0.01 | 100<br>100 |
| (7) CH₃O–P(=S)(–O–[pyrimidine: 4-CH₃, 5-Cl, 6-CH₃])–O–n-C₄H₉ | 0.1<br>0.01 | 100<br>98 |
| (1) (C₂H₅O)₂P(=S)–O–[pyrimidine: 4-CH₃, 5-Cl, 6-CH₃] | 0.1<br>0.01 | 100<br>100 |
| (5) (C₂H₅O)₂P(=O)–O–[pyrimidine: 4-CH₃, 5-Cl, 6-CH₃] | 0.1<br>0.01 | 100<br>100 |
| (2) C₂H₅O–P(=S)(–O–[pyrimidine: 4-CH₃, 5-Cl, 6-CH₃])–O–n-C₃H₇ | 0.1<br>0.01 | 100<br>100 |
| (3) C₂H₅O–P(=S)(–O–[pyrimidine: 4-CH₃, 5-Cl, 6-CH₃])–S–n-C₃H₇ | 0.1<br>0.01 | 100<br>100 |
| (4) C₂H₅O–P(=S)(–O–[pyrimidine: 4-CH₃, 5-Cl, 6-CH₃])–NH–iso-C₃H₇ | 0.1<br>0.01 | 100<br>100 |

EXAMPLE 5

Critical concentration test/soil insects I

Test insect: *Phorbia antiqua* — grubs in the soil
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with the soil. The concentration of the active compound in the preparation was practically immaterial, the only decisive factor being the amount by weight of active compound per unit volume of soil, which is quoted in ppm (= mg/l). The soil was filled into pots and the pots were left to stand at room temperature.

After 24 hours the test insects were introduced into the treated soil and after a further 2 to 7 days the degree of effectiveness of the active compound was determined in % by counting the dead and live test insects. The degree of effectiveness is 100% if all test insects had been killed and is 0% if exactly as many test insects were still alive as in the case of the untreated control.

The active compounds, amounts used and results can be seen from the table which follows:

Table 5

(*Phorbia antiqua* grubs in the soil)

| Active compound | Degree of destruction in % at an active compound concentration of 5 ppm |
|---|---|
| 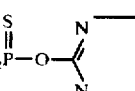 (known) (B) | 0 |
| 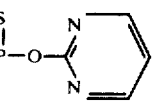 (known) (A) | 0 |
| 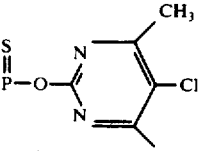 (1) | 100 |
| (2) | 100 |
| (3) | 100 |
| (6) | 100 |
| (7) | 100 |

Table 5-continued (*Phorbia antiqua* grubs in the soil)

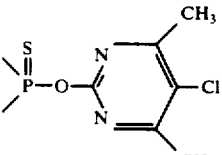

EXAMPLE 6

Critical concentration test/soil insects II

Test insect: *Meloidogyne incognita*
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with the soil. The concentration of the active compound in the preparation was practically immaterial, the only decisive factor being the amount by weight of active compound per unit volume of soil, which was quoted in ppm (= mg/l). The soil was filled into pots and the pots were left to stand at room temperature.

After 24 hours the test insects were introduced into the treated soil and after a further 2 to 7 days the degree of effectiveness of the active compound was determined in % by counting the dead and live test insects. The degree of effectiveness is 100% if all test insects had been killed and is 0% if exactly as many test insects were still alive as in the case of the untreated control.

The active compounds, amounts used and results can be seen from the table which follows:

Table 6

(*Meloidogyne incognito*)

| Active compound | Degree of destruction in % at an active compound concentration of 5 ppm |
|---|---|
| 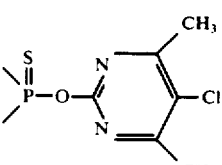 (known) (B) | 0 |
| 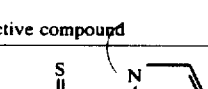 (known) (A) | 0 |

Table 6-continued (*Meloidogyne incognito*)

| Active compound | Degree of destruction in % at an active compound concentration of 5 ppm |
|---|---|
| (C₂H₅O)₂P(=S)—O—[4,6-dimethyl-5-chloro-pyrimidin-2-yl] (1) | 100 |
| C₂H₅O, n-C₃H₇O — P(=S)—O—[4,6-dimethyl-5-chloro-pyrimidin-2-yl] (2) | 100 |
| C₂H₅O, n-C₃H₇S — P(=S)—O—[4,6-dimethyl-5-chloro-pyrimidin-2-yl] (3) | 100 |
| CH₃O, n-C₃H₇O — P(=S)—O—[4,6-dimethyl-5-chloro-pyrimidin-2-yl] (6) | 100 |

EXAMPLE 7

Critical concentration test/nematodes

Test nematode: *Tenebrio molitor* — larvae in the soil
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with soil which was heavily infested with the test nematodes. The concentration of the active compound in the preparation was of practically no importance; only the amount of active compound per unit volume of soil, which is given in ppm, was decisive. The treated soil was filled into pots, lettuce was sown in the pots were kept at a greenhouse temperature of 27° C.

After 4 weeks, the lettuce roots were examined for infestation with nematodes (root galls), and the degree of effectiveness of the active compound was determined as a percentage. The degree of effectiveness is 100% when infestation was completely avoided; it is 0% when the infestation was exactly the same as in the case of the control plants in untreated soil which had been infested in the same manner.

The active compounds, the amounts applied and the results can be seen from the following table:

Table 7

(*Tenebrio molitor* - larvae in the soil)

| Active compound | Degree of destruction in % at an active compound concentration of 5 ppm |
|---|---|
| (C₂H₅O)₂P(=S)—O—[pyrimidin-2-yl] (known) (B) | 0 |
| (CH₃O)₂P(=S)—O—[pyrimidin-2-yl] (known) (A) | 0 |
| (C₂H₅O)₂P(=S)—O—[4,6-dimethyl-5-chloro-pyrimidin-2-yl] (1) | 100 |
| C₂H₅O, n-C₃H₇O — P(=S)—O—[4,6-dimethyl-5-chloro-pyrimidin-2-yl] (2) | 100 |
| C₂H₅O, n-C₃H₇S — P(=S)—O—[4,6-dimethyl-5-chloro-pyrimidin-2-yl] (3) | 100 |
| CH₃O, n-C₃H₇O — P(=S)—O—[4,6-dimethyl-5-chloro-pyrimidin-2-yl] (6) | 100 |
| CH₃O, n-C₄H₉O — P(=S)—O—[4,6-dimethyl-5-chloro-pyrimidin-2-yl] (7) | 100 |

The process of this invention is illustrated in the following preparative Examples.

EXAMPLE 8 a. The hydrochloride of 2-hydroxy-4,6-dimethyl-5-chloro-pyrimidine (III), required as the starting material, could be prepared as follows:

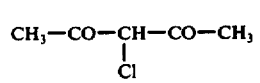
(i)

A solution of 283 g (2.1 moles) of sulfuryl chloride in 300 ml of methylene chloride was added dropwise at 20°–30° C to a solution of 200 g (2 moles) of pentane-2,4-dione in 1,000 ml of methylene chloride. The mixture was additionally heated for 3 hours under reflux; the solvent was then distilled off and the residue was distilled in vacuo. 235 g (87.5% of theory) of 3-chloropentane-2,4-dione were obtained as a colorless oil of boiling point 78° C/12 mm Hg.

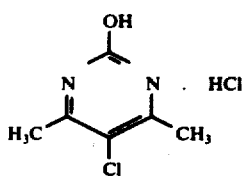

(ii)

A solution of 134.5 g (1 mole) of the 3-chloropentane-2,4-dione prepared as in (i) and 75 g (1.25 moles) of urea in 800 ml of ethanol and 100 ml of concentrated hydrochloric acid was heated for 10 hours under reflux. It was then cooled to −10° C, whereupon a precipitate formed, which was filtered off and dried. 114 g (58% of theory of 2-hydroxy-5-chloro-4,6-dimethylpyrimidine hydrochloride were obtained in the form of colorless crystals of melting point >210° C.

b) 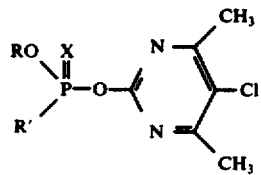 (I)

18.8 g (0.1 mole) of O,O-diethylthionophosphoric acid diester chloride were added dropwise to a suspension of 19.6 g (0.1 mole) of 2-hydroxy-5-chloro-4,6-dimethylpyrimidine hydrochloride and 29 g (0.21 mole) of potassium carbonate in 200 ml of acetonitrile. The reaction mixture was heated to 40° C for 4 hours and then cooled and poured into 300 ml of toluene. The mixture was twice extracted by shaking with water and the organic phase was separated off and dried over sodium sulfate. The solvent was then stripped off in vacuo and the residue was subjected to slight distillation at 100° C. 20 g (65% of theory) of O,O-diethyl-O-[4,6-dimethyl-5-chloropyrimidin (2)yl]-thionophosphoric acid ester were obtained in the form of a yellow oil having a refractive index $n_D^{24}$ of 1.5129.

The following compounds of the general formula

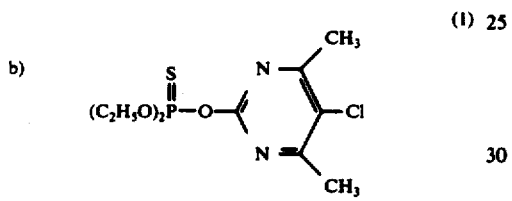

(I)

could be prepared analogously:

| Compound No. | X | R | R' | Yield (% of theory) | Refractive index: |
|---|---|---|---|---|---|
| 2 | S | $C_2H_5$ | $OC_3H_7$—n | 68 | $n_D^{22}$ : 1.5308 |
| 3 | S | $C_2H_5$ | $SC_3H_7$—n | 20 | $n_D^{22}$ : 1.5370 |
| 4 | S | $C_2H_5$ | $NH—C_3H_7$—iso | 40 | $n_D^{22}$ : 1.5143 |
| 5 | O | $C_2H_5$ | $OC_2H_5$ | 51 | $n_D^{22}$ : 1.4792 |
| 6 | S | $CH_3$ | $OC_3H_7$—n | 36 | $n_D^{22}$ : 1.5175 |
| 7 | S | $CH_3$ | $OC_4H_9$—n | 31 | $n_D^{22}$ : 1.5207 |

Other compounds which can be similarly prepared include:
O,S-di-n-butyl-O-[4,6-dimethyl-5-chloropyrimidin(2-)yl]-thionothiolphosphoric acid ester,
O,N,N-tri-n-propyl-O-[4,6-dimethyl-5-chloropyrimidin(2)yl]-thionophosphoric acid ester-amide,
O,O-dimethyl-O-[4,6-dimethyl-5-chloropyrimidin(2-)yl]-phosphoric acid ester,
O-ethyl-N,N-dimethyl-O-[4,6-dimethyl-5-chloropyrimidin(2)yl]-phoshoric acid ester-amide,
and the like.

It will be appreciated that the instant specification and examples are set forth by way of illustration and not limitation, and that various modifications and changes may be made without departing from the spirit and scope of the present invention.

What is claimed is:

1. An O-alkyl-O-[4,6-dimethyl-5-chloropyrimidin(2-)yl]-(thiono) (thiol)phosphoric acid ester of the formula

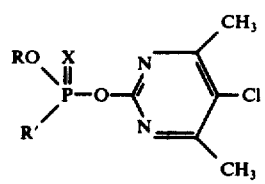

in which
R is alkyl with 1 to 6 carbon atoms,
R' is alkoxy or alkylthio with 1 to 6 carbon atoms in each alkyl chain, and
X is oxygen or sulfur.

2. A compound according to claim 1, in which R is straight-chain or branched alkyl with 1 to 4 carbon atoms and R' is straight-chain or branched alkoxy with 1 to 5 carbon atoms or straight-chain or branched alkylthio with 1 to 4 carbon atoms.

3. The compound according to claim 1 wherein such compound is O,O-diethyl-O-[4,6-dimethyl-5-chloropyrimidin(2)yl[-thionophosphoric acid ester of the formula

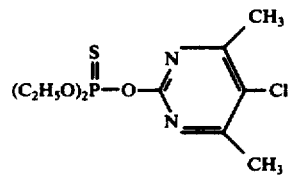

4. The compound according to claim 1 wherein such compound is O-ethyl-O-n-propyl-O-[4,6-dimethyl-5-chloropyrimidin(2)yl[-thionophosphoric acid ester of the formula

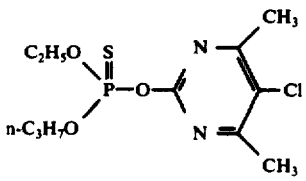

5. The compound according to claim 1 wherein such compound is O-ethyl-S-n-Propyl-O-[4,6-dimethyl-5- chloropyrimidin(2)yl]-thionothiolphosphoric acid ester of the formula

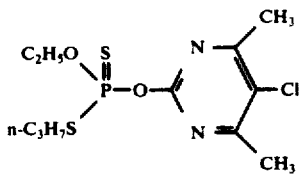

6. The compound according to claim 1 wherein such compound is O-methyl-O-n-propyl-O-[4,6-dimethyl-5-chloropyridin(2)yl]-thionophosphoric acid ester of the formula

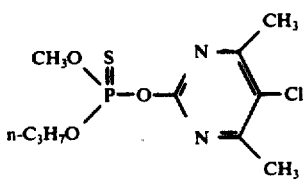

7. The compound according to claim 1 wherein such compound is O-methyl-O-n-butyl-O-[4,6-dimethyl-5-chloropyrimidin(2)yl[-thionophosphoric acid ester of the formula

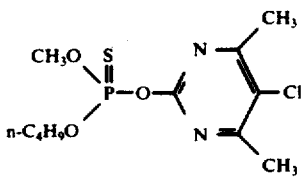

8. An insecticidal, acaricidal or nematicidal composition containing as active ingredient an insecticidally, acaricidally or nematicidally effective amount of a compound according to claim 1 in admixture with a diluent.

9. A method of combating insects, acarids or nematodes which comprises applying to the insects, acarids or nematodes or to a habitat thereof an insecticidally, acaricidally or nematicidally effective amount of a compound according to claim 1.

10. The method according to claim 9 in which said compound is
O,O-diethyl-O-[4,6-dimethyl-5-chloropyrimidin(2-)yl]-thionophosphoric acid ester,
O-ethyl-O-n-propyl-O-[4,6-dimethyl-5-chloropyrimidin(2)yl ]-thionophosphoric acid ester,
O-ethyl-S-n-propyl-O-[4,6-dimethyl-5-chloropyrimidin(2)yl]-thiionothiolphosphoric acid ester,
O-methyl-O-n-propyl-O-[4,6-dimethyl-5-chloropyrimidin(2)yl]-thionophosphoric acid ester, or
O-methyl-O-n-butyl-O-[4,6-dimethyl-5-chloropyrimidin(2)yl]-thionophosphoric acid ester.

* * * * *